US006852864B2

(12) United States Patent
Naik et al.

(10) Patent No.: US 6,852,864 B2
(45) Date of Patent: Feb. 8, 2005

(54) PROCESS FOR THE SYNTHESIS OF DIPYRROMETHANES

(75) Inventors: Rajan Hiralal Naik, Maharashtra (IN); Padmakar Laxman Joshi, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/113,229

(22) Filed: Mar. 28, 2002

(65) Prior Publication Data

US 2003/0187278 A1 Oct. 2, 2003

(51) Int. Cl.⁷ .................... C07D 207/00; C07D 207/323
(52) U.S. Cl. ...................................... 548/518; 548/564
(58) Field of Search ................................ 548/518, 564

(56) References Cited

U.S. PATENT DOCUMENTS 5,883,246 A    3/1999  Bruckner et al. ........... 540/145
5,919,923 A  * 7/1999  Bruckner et al. ........... 540/145

OTHER PUBLICATIONS

Lee CH, Lindsey JS. One–flask synthesis of meso–substituted dipyrromethanes and their application in the synthesis of trans–substituted porphyrin building blocks. Tetrahedron 1999;50:11427–40.*

C.H. Lee et al., *Tetrahedron*, 1995, 51(43):11645–11672.

D.M. Wallace et al., *J. Org. Chem.*, 1993, 58(25):7245–7257.

J.C. Sessler et al., *J Amer. Chem. Soc.*, 1993, 115(11):4618–4628.

R.K. Pandey et al., *Tetrahedron Letters*, 1992, 33(37):5315–5318.

* cited by examiner

*Primary Examiner*—Deborah C. Lambkin
(74) *Attorney, Agent, or Firm*—Morgan & Finnegan, LLP

(57) ABSTRACT

The present invention provides an improved method for the preparation of dipyrromethanes by reacting the pyrrole with an aldehyde in the presence of an cation exchange resin.

5 Claims, No Drawings

PROCESS FOR THE SYNTHESIS OF DIPYRROMETHANES

FIELD OF THE INVENTION

The present invention relates to a process for the synthesis of dipyrromethanes of formula 1 below:

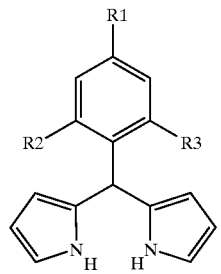

wherein R1, R2 and R3 are selected from hydrogen, alkyl, halo, nitro and amine groups.

More particularly the present invention relates to a process for the synthesis of dipyrromethanes by the condensation of pyrrole with various aldehydes.

BACKGROUND OF THE INVENTION

Dipyrromethanes (fragments containing two pyrrole units) are crucial intermediates for the synthesis of porphyrins, such as meso-substituted core modified porphyrins and their use in oxidative reactions of organic substrates are of interest in porphyrin model system studies and such compounds have shown potential as industrial catalyst.

The process presented here shows wide applicability for the preparation of 5, 10, 15, 20-tetra aryl substituted porphyrins with two-fold rotation symmetry. In the prior art, these meso-substituted dipyrromethanes have been prepared by any of the following procedures. 1. By acid catalyzed condensation of pyrrole and aldehyde in suitable solvents such as dichloromethane (Homogenous conditions), where the acid catalysts employed are trifluoroacetic, acid, propionic acid (neat), TiCl$_4$, BF$_3$—Etherate, etc. (References: Lee. C. H, Li, F. Iwamoto N; Dadok, J; Bothner-By, A. A; *J. S Tetrahedron.* 1995,51,11,645.2; Wallace, D. M; Leung, S. H.; Senge, M. O.; Smith K. M. *J. Org. Chemistry,* 1993,58,7245.3; Sessler, J. C. Capuano V. C., Harriman, A.J. *Am. Chem. Soc.* 1993, 115,4618.4; Pandey, R. K., Forsyth, T. P., Gerzevske. K. R., Lin, J. J., Smith K. M., *Tetrahedron Lett.* 1992,33,5315). In all the above references the use of resins has not been mentioned.

U.S. Pat. Nos. 5,919,923 and 5,883,246 (both 1999) describe the synthesis of tripyrranes in which dipyrromethanes are obtained as a by-product. Although these patents mention probable use of resins as catalysts, there is no example illustrating the use of resins. The entire specification emphasizes the use of strong Lewis acids. The use of strong Lewis acids provides tripyrranes because of the strong acidity. Because of the strong acidity there is no control as the formation of the products. The above mentioned patents primarily describe the process for preparation of tripyrranes with a small amount of dipyrromethanes as by-products.

It has been observed that if weak Lewis acids such as resins are used instead of strong Lewis acids the selectivity for dipyrromethanes is very high because of controlled acidity. However, prior art processes suffer from several disadvantages such as:

(a) Formation of oligomers due to homogenous acidic conditions along with dipyrromethanes.
(b) Variations in the yields of dipyrromethanes in case of acid sensitive aldehydes.
(c) Involves complex work-up followed by stringent column chromatorgraphy to get pure dipyrromethane.

OBJECTS OF THE INVENTION

The main object of the invention is to provide a modified process for the preparation of dipyrromethanes, which overcomes the aforesaid drawbacks.

It is another object of the invention to provide a process for the preparation of dipyrromethanes with improved yield.

It is a further object of the invention to provide a process for the preparation of dipyrromethanes which results in simple work up procedure and is therefore economical and efficient.

SUMMARY OF THE INVENTION

The above and other objects of the invention are achieved by the process of the present invention which uses cation exchange resins as catalysts.

Accordingly, the present invention provides a process for the synthesis of dipyrromethanes of formula 1:

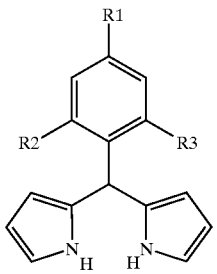

wherein R1, R2 and R3 are selected from hydrogen, alkyl, halo, nitro and amine groups, said process comprising reacting an aromatic aldehyde and pyrrole in the presence of an acid catalyst comprising a cation exchange resin at a temperature in the range of 10 to 30° C. in an organic solvent for a period in the range of 30 to 60 minutes, filtering the resin and evaporating the solvent to obtain the dipyrromethane.

In one embodiment of the invention, R1 is selected from the group consisting of H, Cl, Br, CH$_3$, OCH$_3$, OH and NO$_2$, R2 and R3 are both independently selected from H and Cl.

In another embodiment of the invention, the yield of the dipyrromethane is in the range of 75 to 85%.

In another embodiment of the invention, the aldehyde comprises a substituted aldehyde with the substituents comprising one to two substituting groups, which may be the same or different and are selected from alkyl, nitro, halo, amino and hydroxy.

In a further embodiment of the invention, the aldehyde is selected from the group consisting of benzaldehyde, 2,6,-dichlorobenzaldehye, 4-chlorobenzaledhyde, 4-hydroxybenzaldehyde, anisaldehyde and salycilaldehyde.

In another embodiment of the invention, organic solvent is selected from the group consisting of dichloromethane, dichloroethane, chloroform, benzene, toluene and acetonitrile.

In yet another embodiment of the invention, the cation exchange resin is selected from the group consisting of Amberlyst-15, Tulsion-T42 and Indion-130.

DETAILED DESCRIPTION OF THE INVENTION

There is a need to improve the dipyrromethane yields, which in turn gives tetraaryl porphyrins in higher conversions. The present invention describes the improved process of dipyrromethane in high yields simple work up procedure, which subsequently affords better yields of commercially important porphyrins. The present invention provides a process for preparing mesosubstituted dipyrromethanes wherein R1, R2, and R3 are each independently selected from hydrogen, alkyl, halo, nitro and amine groups, by reacting an aromatic aldehyde and pyrrole in the presence of an acid catalyst comprising a cation exchange resin. The reaction is preferably done at a temperature in the range of 10 to 30° C. in an organic solvent for a period in the range of 30 to 60 minutes, filtering the resin and evaporating the solvent to obtain the dipyrromethane. R1 is selected from the group consisting of H, Cl, Br, $CH_3$, $OCH_3$, OH and $NO_2$, R2 and R3 are both independently selected from H and Cl. The yield of the dipyrromethane is in the range of 75 to 85%. The aldehyde is preferable a substituted aldehyde with the substituents comprising one to two substituting groups, which may be same or different and are selected from hydrogen, alkyl, halo, nitro and amino and hydroxy.

The aldehyde is preferably selected from benzaldehyde, 2,6,-dichlorobenzaldehye, 4-chlorobenzaledhyde, 4-hydroxybenzaldehyde, anisaldehyde and salycilaldehyde. The organic solvent used can be any conventional organic solvent such as dichloromethane, dichloroethane, chloroform, benzene, toluene or acetonitrile and the like. The cation exchange resin is selected from the group consisting of Amberlyst-15, Tulsion-T42 and Indion-130. Following this viable synthetic route, a wide spectrum of porphyrins and metalloporphyrins can be synthesized.

The advantages of the present invention are as follows:
(1). Due to heterogeneous nature of acid catalyst formation of unwanted oligomers viz. tripyrromethanes, etc. are substantially eliminated.
(2). Easy work-up includes only filtration and removal of solvent after the reaction, affording pure dipyrromethanes in better yields compared to reported procedures.
(3). No separate purification methods such as column chromatography are required.

The invention described herein below by the examples, which are illustrative only and should not be construed to limit the scope of the present invention.

EXAMPLE 1

Preparation of Mesophenyl Dipyrromethane

A cation exchange resin (Amberlyst 15, 1 g) in 80 ml of dichloromethane was taken to which benzaldehyde (0.488 g, 4.30 mmole) was added and degassed by bubbling with argon for 10 minutes, stirred for 10 minutes. Freshly distilled pyrrole (3 ml, 43 mmole) was added drop wise and stirred at room temperature for 40 minutes. Reaction was monitored by TLC. Dark pink spot on TLC shows formation of dipyrromethane. The reaction mixture was filtered and dichloromethane was evaporated and excess pyrrole was removed by vacuum distillation, furnishing a brownish solid. Yield: (0.696 g, 73%), base m/e 145 (molecular ion peak: 290).

EXAMPLE 2

Preparation of Meso (2,6-dichlorophenyl) Dipyrromethane

To the mixture of cation exchange resin (Tulsion T-40, 1.5 g) in 100 ml dichloromethane, 2,6-dichlorobenzadehyde (0.458 g, 4.3 mole) was added and degassed by bubbling with argon for 10 minutes. Freshly distilled pyrrole (3 ml, 43 mmole) was added drop wise and stirred at room temperature for 1 hr. After the reaction was over, it was worked up, as described earlier, to give solid (0.98 g, 78.4%).

EXAMPLE 3

Preparation of Meso(4-chlorophenyl) Dipyrromethane

To the degassed mixture of 4-chlorobenzaldehyde (0.602 g, 4.30 mmol) and freshly distilled pyrrole (5 ml, 86 mmole) in 60 ml of dichloromethane, cation exchange resin (Indion-130, 1.2 g) was added and stirred for 45 minutes. Dark pink sport on TLC showed the formation for dipyrromethane. The reaction mixture was worked up, as described earlier, to give brownish solid (0.97 g, 88%).

We claim:

1. A process for preparation of mesosubstituted dipyrromethanes of the formula:

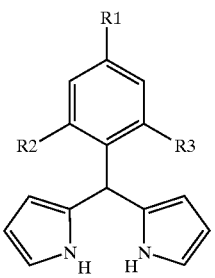

wherein R1, R2 and R3 are selected from hydrogen, alkyl, halo, nitro and amine groups, said process comprising reacting an aromatic aldehyde and pyrrole wherein the mole ratio of pyrrole:aromatic aldehyde is in the ratio of 10:1 to 20:1 in the presence of an acid catalyst comprising a cation exchange resin selected from a group consisting of Amberlyst-15, Tulsion-T42 and Indion-130 at a temperature in the range of 10 to 30° C. in an organic solvent for a period in the range of 30 to 60 minutes, filtering the resin and evaporating the solvent to obtain a yield in the range of 73% to 88% of dipyrromethane.

2. A process as claimed in claim 1 wherein R1 is selected from the group consisting of H, Cl, Br, $CH_3$, $OCH_3$, OH, and $NO_2$, R2 and R3 are both independently selected from H and Cl.

3. A process as claimed in claim 1 wherein the aldehyde comprises a substituted aldehyde with the substituents comprising one to two substituting groups, which may be the same or different and are selected from alkyl, nitro, halo, amino and hydroxy.

4. A process as claimed in claim 1 wherein the aldehyde is selected from the group consisting of benzaldehyde, 2,6,-dichlorobenzaldehyde, 4-chlorobenzaldehyde, 4-hydroxybenzaldehyde and salycilaldehyde.

5. A process as claimed in claim 1 wherein the solvent is selected from the group consisting of dichloromethane, dichloroethane, chloroform, benzene, toluene and acetonitrile.

* * * * *